United States Patent [19]
Kornetsky

[11] Patent Number: 6,153,620
[45] Date of Patent: Nov. 28, 2000

[54] OPIATE RECEPTOR ANTAGONIST MODULATES MOVEMENT DISORDER

[75] Inventor: Conan Kornetsky, Lexington, Mass.

[73] Assignee: Trustees of Boston University, Boston, Mass.

[21] Appl. No.: 08/006,691

[22] Filed: Jan. 21, 1993

Related U.S. Application Data

[63] Continuation of application No. 07/660,543, Feb. 25, 1991, abandoned.
[51] Int. Cl.⁷ .......................... A61K 31/44; A61K 31/34; A61K 31/535
[52] U.S. Cl. .......................... 514/282; 514/468; 514/471; 514/229.5
[58] Field of Search .................................. 514/282, 468, 514/471, 229.5; 424/10

[56] References Cited

PUBLICATIONS

Webster *Dictionary* p. 763, 1990.
Cadet et al. "Naltrexone Inhibits..." *Neuropeptides* 8(1) 87–91 (1986) Abstracted Chem Abs 105(17):146140 (1986).
D.R. Burt, I. Creese, S.H. Snyder, "Antischizophrenic Drugs: Chronic Treatment Elevates Dopamine Receptor Binding in Brain", Jul. 7, 1976, revised Oct. 6, 1976, Science vol. 196, pp. 326–328.
M.D. Hall, P. Jenner, C.D. Marsden, N.M.J. Rupniak, "Short Term Changes in Cerebral Dopamine Receptor Function During Continuous Haloperidol Administration", (1982) British Journal of Pharmacology, vol. 76 p. 233P.
P. Muller, P. Seeman, "Dopaminergic Supersensitivity After Neuroleptics; Time–Course and Specificity", Psychopharmacology 60. 1–11 (1978) pp. 1–11.
P. McGonigle, S. Boyson, S. Reuter, P. Molinoff, "Effects of Chronic Treatment with Selective and Nonselective Antagonists on the Subtypes of Dopamine Receptors", SYNAPSE 3:74–82 (1989) pp. 74–82.
C.A. Wilmot, A.M. Szczepanik, "Effects of acute and chronic treatments with clozapine and haloperidol on serotonin (5–HT2) and dopamine (D2) receptors in the rat brain", Brain Research 487 (1989), pp. 288–298.
J.L. Waddington, A.J. Cross, S.J. Gamble, R.C. Bourne, "Spontaneous Orofacia Dyskinesia and Dopaminergic Function in Rats After 6 Months of Neuroleptic Treatment", Apr. 29, 1983, Science, vol. 220, pp. 530–532.
H.L. Klawans, Jr., R. Rubovits, "An Experimental Model of Tardive Dyskinesia", Journal of Neural Transmission (1972) pp. 235–246.
B. Weiss, S. Santelli, G. Lusnik, "Movement Disorders Induced in Monkeys by Chronic Haloperidol Treatment", Psychopharmacology, Received Feb. 10, 1976; Final Version Jan. 11, 1977; pp. 289–293.
D. Tarsy, R.J. Baldessarini, "Behavorial Supersensitivity to Apomorphine Following Chronic Treatment with Drugs Which Interfere with the Synaptic Function of Catecholamines", Neuropharmacology, 1974, pp. 927–940.
G. Ellison, P. Johansson, E. Levin, R. See, L. Gunne, "Chronic neuroleptics alter the effects of the D1 agonist SK&F 38393 and the D2 agonist LY171555 on oral movements in rats", Psychopharmacology (1988), Received Jul. 14, 1987; Final version May. 10, 1988; pp. 253–257.
G. Ellison, R. See, "Rats administered chronic neuroleptics develop oral movements which are similar in form to those in humans with tardive dyskinesia", Psychopharmacology, Received Mar. 6, 1989; Final version Mar. 6, 1989, pp. 564–566.
J.G. Nutt, A.J. Rosin, T. Eisler, D.B. Caine, T.N. Chase, "Effect of an Opiate Antagonist on Movement Disorders", 1978 Arch. Neurol., vol. 35 pp. 810–811.
J.S. Schneider, "Role of the Basal Ganglia in a Chemically Induced Dykinesia in Rat", (1984) Experimental Neurology, vol. 84, pp. 524–532.
J.L. Cadet, T.L. Braun, "Naltrexone Inhibits the Persistent Spasmodic Dyskinesia Induced by Chronic Intraperitoneal Administration of Iminodipropionitrile (IDPN)", (1986) Neuropeptides, vol. 8, pp. 87–91.
J.P. Lindenmayer, E. Gardner, E. Goldberg, L.A. Opier, S.R. Kay, H.M. van Praag, M. Weiner, St. Zukin, "High–Dose Naloxone in Tardive Dyskinesia", (1988), Psychiatry Research, Vo. 26, pp. 19–28.
R. Sandyk, S.R. Snider, "Naloxone Treatment of L–Dopa–Induced Dyskinesias in Parkinson's Disease", (1986) American Journal of Psychiatry, vol. 143, p. 118.
J. Volavka, B. Anderson, G. Koz, "Naloxone and Naltrexone in Mental Illness and Tardive Dyskinesia", (1982), Annuals N.Y. Acad. Science, vol. 398, pp. 97–102.

*Primary Examiner*—Theodore J. Criares
*Attorney, Agent, or Firm*—Choate, Hall & Stewart

[57] ABSTRACT

A method for modulating onset of tardive dyskinesia in a subject includes the step of administering to the subject an opiate receptor antagonist concomitantly with the neuroleptic. Also, a method for modulating a genetic or idiopathic or psychogenic hyperkinetic movement disorder, such as that characteristic of Huntington's Disease, includes the step of administering to the subject an opiate receptor antagonist.

17 Claims, No Drawings

OPIATE RECEPTOR ANTAGONIST MODULATES MOVEMENT DISORDER

This is a continuation of application(s) Ser. No. 07/660,543 filed on Feb. 25, 1991 now abandoned.

This invention was made in the course of work supported in part by U.S. Government funds, and the Government has certain rights in the invention.

BACKGROUND OF THE INVENTION

This invention relates to treatment of hyperkinetic movement disorders such as, for example, tardive dyskinesia and the hyperkinesia associated with Huntington's Disease. Tardive dyskinesia ("TD") is an extrapyramidal hyperkinetic movement disorder that appears in some patients being treated by administration of certain antipsychotic agents ("neuroleptics"). A progressive dyskinesia ("chorea") is characteristic of Huntington's Disease ("HD").

Hyperkinetic movement disorders are characterized by non-purposeful, repetitive, disordered motor acts, variously termed "compulsive", "convulsive", "rhythmical", or "stereotyped". The term "stereotypy" refers here to a repeated behavior that appears repetitively with slight variation or, less commonly, as a complex series of movements. In humans stereotypies can be psychogenic (e.g., tics), idiopathic (as in, e.g., Tourette's syndrome and Parkinson's Disease, genetic (as in, e.g., the chorea characteristic of Huntington's Disease), infectious (as in, e.g., Sydenham's Chorea), or, as in TD, drug-induced.

The most generally accepted theory of the etiology of TD is that chronic administration of the neuroleptic (typically, for example, a butyrophenone such as haloperidol, or a phenothiazine such as fluphenazine) results in a postsynaptic dopamine receptor supersensitivity. Evidence for such supersensitivity comes from receptor binding studies showing specific changes in striatal dopamine receptors (see, e.g., Burt et al. (1977), *Science*, Vol. 196, pp. 326–28; Muller et al. (1978), *Psychopharmacology*, Vol. 60, pp. 1–11; and, more recently, McGonigle et al. (1989), *Synapse*, Vol. 3, pp. 74–82; and Wilmot et al. (1989), *Brain Res.*, Vol. 487, pp. 288–298); and behavioral studies which have focused on the production of oral stereotypic behaviors resulting from chronic dopamine antagonist treatment alone (Weiss et al. (1977), *Psychopharmacology*, Vol. 53, pp. 289–93; Waddington et al. (1983), *Science*, Vol. 220, pp. 530–32). The oral stereotypy produced by chronic neuroleptic treatment in animals has been described as almost identical in physical character to that seen in humans (Ellison et al. (1989), *Psychopharmacology*, Vol. 98, pp. 564–66). Because spontaneous oral dyskinesias are uncommon in animals receiving neuroleptics (Kawans et al. (1972), *Jour. Neural Trans.*, Vol. 33, pp. 235–46), the administration of a dopamine agonist following two to three weeks of neuroleptic treatment results in an oral stereotypy (Tarsy et al. (1974), *Neuropharmacology*, Vol. 13, pp. 927–40; Ellison et al. (1988), *Psychopharmacology*, Vol. 96, pp. 253–57) that has become a widely used animal model of TD (Hall et al. (1982), *British Jour. Pharmacol.*, Vol. 76, p. 233P).

At present opiate antagonists are in use principally in urban emergency care settings, where they are administered to reverse effects of an overdose of heroin or morphine. Naloxone (marketed for example as Narcan®), the opiate antagonist most often used for this purpose, has a short duration of action, and must be administered parenterally. Naltrexone (marketed for example as Trexan®), an opiate antagonist that is longer acting than naloxone and can be orally administered, was introduced more recently. Naltrexone is in use principally to treat overdose of an opiate drug, and to treat persons who are physically dependent on opiate drugs, such as, e.g., heroin. Daily administration of naltrexone completely blocks the euphoric effects of opiate agonists such as morphine or heroin, and if administered to persons who are physically dependent on opiate drugs naltrexone precipitates withdrawal.

SUMMARY OF THE INVENTION

I have discovered that administration of an opiate receptor antagonist can be effective in modulating hyperkinetic movement disorders in mammals. Administration of an opiate receptor antagonist to a subject mammal can prevent and can block neuroleptic-mediated oral stereotypies in the subject.

Concomitant administration of an opiate receptor antagonist with a neuroleptic can prevent neuroleptic-induced onset of tardive dyskinesia.

In general, one aspect, the invention features a method for modulating onset of tardive dyskinesia in a subject, by administering to the subject an opiate receptor antagonist concomitantly with the neuroleptic. The opiate receptor antagonist is administered "concomitantly", as that term is used here, if it is administered in a time commencing prior to commencement of a time in which the neuroleptic is administered, and if the neuroleptic and the opiate receptor antagonist are administered at least partly concurrently.

In preferred embodiments the opiate receptor antagonist includes naltrexone; the opiate receptor antagonist includes naloxone; the opiate receptor antagonist is administered to the subject parenterally; the opiate receptor antagonist is administered to the subject orally; administration of the opiate receptor antagonist to the subject commences prior to or at the same time as an administration of the neuroleptic commences. Preferably, where administration of the opiate receptor antagonist precedes administration of the neuroleptic, administration of the neuroleptic commences within the operative time (or active time) of the particular opiate receptor antagonist under the conditions of administration. In treating humans, naloxone is administered (typically parenterally) preferably within an hour prior to administration of the neuroleptic; and naltrexone is administered (typically orally) preferably within two hours prior to administration of the neuroleptic.

In another general aspect, the invention features a method for modulating a genetic or idiopathic or psychogenic hyperkinetic movement disorder by administering to the subject an opiate receptor antagonist.

In preferred embodiments the subject has Huntington's Disease or is predisposed to Huntington's Disease; the opiate receptor antagonist includes naltrexone; the opiate receptor antagonist includes naloxone; the opiate receptor antagonist is administered to the subject parenterally; the opiate receptor antagonist is administered to the subject orally.

DESCRIPTION OF PREFERRED EMBODIMENTS

Opiate receptor antagonists can be used according to the invention to treat hyperkinetic movement disorders, as for example to treat tardive dyskinesia or dyskinesia associated with Huntington's Disease. The following examples are presented by way of example.

Method

Generally, the method of the invention can be used for treatment of tardive dyskinesia in a subject, that is, for suppression of TD prior to onset of symptoms of TD as well as for reduction of TD in subjects in which symptoms are already manifest.

EXAMPLES

The examples that follow illustrate the use of the opiate receptor antagonist naloxone to suppress stereotypy in rats. The examples are presented for illustrative purposes only. As will be appreciated, the method according to the invention can be used for treatment of TD in other animals including humans, and other opiate receptor antagonists can be used according to the invention.

Adult male F-344 rats (Charles River, Wilminton, Mass.) weighing approximately 325–350 grams were used in the examples. Animals were individually housed, provided water and food ad libitum, and were maintained on a 12:12 hour light:dark cycle. Administrations of neuroleptics and opiate receptor antagonists and observations of behavior were all carried out during the light portion of the cycle.

Neuroleptics were prepared for administration as follows. Naloxone (Dupont de Nemours), apomorphine (Sigma), d-amphetamine (Sigma), and amfonelic acid (Research Biochemicals Inc.) were dissolved in isotonic saline to a concentration of 1 mg/ml. Haloperidol (McNeil Laboratories) was dissolved in warm 1N tartaric acid and brought to a concentration of 1 mg/ml with isotonic saline. Naloxone, haloperidol, and saline were administered by intraperitoneal injection; and apomorphine, amphonelic acid, and amphetamine were administered by subcutaneous injection.

Example 1
Concomitant Administration of Opiate Receptor Antagonist with Neuroleptic in a Chronic Administration Protocol Prevents Tardive Dyskinesia.

The neuroleptic haloperidol (5.0 mg/kg; 13.3 $\mu$M) was administered to nine rats once daily for 21 days. Twenty minutes prior to each haloperidol injection (that is, in a concomitant administration), each of four of the rats received the opiate receptor antagonist naloxone (16.0 mg/kg; 48.9 $\mu$M), and each of the other five rats received daily injections of saline as a control. Each day during the five hour interval following the treatment, the rats were observed for presence or absence of oral stereotypy in acrylic observation chambers (15×15×30 cm) with horizontal steel floor bars. The rats remained sedated for approximately four hours after each haloperidol injection, and observation over the five hour period permitted approximately one additional hour of observation of the animals in an unsedated condition. None of the nine rats showed any sign of oral stereotypy during any observation period on any of the first 21 days.

After day 21 naloxone-haloperidol and saline-haloperidol administrations were discontinued. On day 22 two rats each from the naloxone-haloperidol and the saline-haloperidol groups received d-amphetamine (2.5 mg/kg; 6.8 $\mu$M), as described generally in Weiss et al. (1988), *Pharmacol. Biochem. Behav.*, Vol. 30, pp. 309–17, and the other five animals received saline (three from the group that had received naloxonehaloperidol, two from the saline-haloperidol group). On day 23 the animals that had received d-amphetamine on day 22 received saline instead, and those that had received saline on day 22 received d-amphetamine instead. On days 24 and 25 the groups of animals were treated as on days 22 and 23, but using apomorphine (0.1 mg/kg; 0.4 $\mu$M), as described generally in Nobrega et al. (1989), *Psychopharmacology*, Vol. 98, pp. 476–82, in place of amphetamine. Following each of these injection with a dopamine agonist or with saline on days 22–25, the animals were placed in acrylic observation chambers as described above, and observed for a three hour period for oral stereotypic behavior. Here, a three hour observation period was sufficient because animals were not sedated by administration of dopamine agonist or saline.

The observation chambers were arranged in a stacked 2×3 arrangement so that the behavior of the animals in all the chambers could readily be observed simultaneously. All observations were made by a trained observer who was unaware of the drugs administered.

Oral stereotypic behavior was defined in these Examples as intense chewing or gnawing over a period of five or more consecutive minutes that was either self-directed or directed at the floor bars of the test chamber.

As Table 1 shows, naloxone administration prior to each haloperidol administration results in failure of d-amphetamine or apomorphine challenge to cause an appearance of oral stereotypy. None of the naloxone-haloperidol treated animals showed any indication of oral stereotypy following injection of the dopamine agonists, whereas all of the animals in the saline-haloperidol group showed significant oral stereotypy. ($p=0.008$, Fisher's exact test 2-tailed naloxone-haloperidol vs. saline-haloperidol.) As

TABLE 1

INCIDENCE OF STEREOTYPY

| | Challenge Treatment | | |
|---|---|---|---|
| Initial Treatment | Amphetamine, 2.5 mg/kg sc | Apomorphine, 0.1 mg/kg sc | Saline |
| Naloxone-Haloperidol | 0 of 4 | 0 of 4 | 0 of 4 |
| Saline-Haloperidol | 5 of 5 | 5 of 5 | 0 of 5 | expected, saline "challenge" resulted in no stereotypy in either treatment group.

The preselected criterion of five minutes of continuous gnawing or chewing behavior was easily met in the saline-haloperidol rats. This oral stereotypy often occurred in bouts of chewing, in many instances exceeding five minutes duration, preceded by and interspersed with intervals of grooming, sniffing, licking, and rearing. The onset of induced stereotypy was within 30 minutes following apomorphine administration and the bouts persisted for 60 minutes or longer. On the other hand, d-amphetamine induced oral stereotypy commenced about two hours after administration of the d-amphetamine, and bouts of chewing continued for all animals for at least 60 minutes, and for some for 2–3 hours after onset. On the amphetamine challenge days both groups of rats showed considerable locomotor activity, marked by head-bobbing and rearing behavior. The amphetamine-induced locomotor activity always preceded the onset of oral stereotypy in the saline-haloperidol group. There did not appear to be a delay in onset of the locomotor activity in the naloxone-haloperidol group. This locomotor activation was not seen following the apomorphine injections.

Example 2
Opiate Receptor Antagonist Blocks Oral Stereotypy Expressed by Dopamine Receptor Agonist.

Haloperidol was administered to five rats (5.0 mg/kg) daily as described in Example 1 for 17 days. Shorter periods of haloperidol treatment are known to be sufficient for expression of dopamine agonist-induced stereotypy (Tarsy et al. (1974)). Because numerous earlier reports have described the oral stereotypy resulting from apomorphine challenge (see, Muller et al. (1978), for review), the selective dopamine receptor agonist amfonelic acid (described in Shore (1976), *Jour. Pharm. Pharmacol.*, Vol. 28, pp. 855–57) was used to elicit stereotypy. On day 18 haloperidol was discontinued and each animal received amfonelic acid (1.0 mg/kg; 3.2 μM) and all animals exhibited oral stereotypy within 15 minutes thereafter, as scored by the above criterion, and once stereotypy was established, three animals received naloxone (16.0 mg/kg) and two received saline. On day 19 amfonelic acid was once again given as on day 18, resulting in similar displays of oral stereotypy; once stereotypy was established the two animals that had received saline on day 18 were given naloxone and the three animals that had received naloxone on day 18 were given saline. On each of days 20–21, the groups of animals were treated as on days 18–19, but using d-amphetamine (2.5 mg/kg) in place of amfonelic acid.

Probability levels were determined by Fisher's exact test, 2 tailed. In Example 1, the statistical analysis compared the incidence of oral stereotypy following amphetamine, apomorphine, or saline challenge in the naloxone-haloperidol group with the incidence of oral stereotypy in the saline-haloperidol group. In Example 2, the analysis compared the antagonism of dopamine agonist-induced oral stereotypy by naloxone to that of saline, as a control.

As shown in Table 2, naloxone reversed the stereotypy in each animal, and this cessation of stereotypy was complete in all animals within 10 minutes after administration of naloxone. ($p=0.008$, Fisher's exact test 2-tailed naloxone-amphetamine vs. saline-amphetamine and naloxone-amphonelic acid vs. saline-amphonelic acid.) This effective antagonism of the oral stereotypy by naloxone was complete and long-lasting, as no

TABLE 2

INCIDENCE OF STEREOTYPY

| | Challenge Treatment | |
|---|---|---|
| Antagonist | Amphetamine, 2.5 mg/kg sc | Amfonelic Acid, 1.0 mg/kg sc |
| Saline, ip | 5 of 5 | 5 of 5 |
| Naloxone, ip | 0 of 5 | 0 of 5 | reappearance of the behavior was observed over an interval of at least 2 hours following naloxone injection.

Administration to rats of haloperidol, a dopamine antagonist, daily for seventeen days or for three weeks, as described in Examples 1 and 2, results in an upregulation of the dopamine receptors, making them more sensitive to dopamine agonists. Thus, after extended daily haloperidol treatment (three weeks or less, see, Tarsy, et al. (1974)) administration of a low dose of d-amphetamine or other dopamine agonist results in oral stereotypic behavior. As Tables 1 and 2 show, not only can this behavior be blocked by naloxone but if the naloxone is administered prior to receiving the dopamine antagonist the stereotypic behavior is never expressed.

Example 3

In the absence of previous haloperidol administration neither d-amphetamine nor apomorphine causes oral stereotypy at the doses used in Examples 1 and 2.

Each of four drug-naive rats was administered d-amphetamine and apomorphine at different times, and observed as described above for the incidence of oral stereotypy. No stereotypy was seen. Knapp et al. (1989), *Pharmacol. Biochem. Behav.*, Vol. 32, pp. 977–82, reported that amfonelic acid (1.0 mg/kg) does not induce oral stereotypic behaviors in drug-naive rats.

Daily high doses of morphine provide a useful model for the study of dyskinesias such as that characterizing Huntington's Disease ("HD"). The following example illustrates a morphine dosage regime that can be used to set up such a model. I have discovered, using such a model system of morphine-induced stereotypy, that re-expression of the stereotypy resulting from chronic morphine administration, whether by a low dose of morphine or by a dopamine agonist, can be blocked by a dopamine antagonist and can be blocked by naloxone.

Example 4

Briefly, morphine administered in three high doses in a 24 hour period can cause oral stereotypy in the rat. The effect of repeated daily high-dose morphine administration is cumulative; that is, a small percentage of rats may display oral stereotypy after a first high dose, a much greater percentage displays oral stereotypy after a second high dose the following day, and oral stereotypy is established after a third high dose on the third day. Once established, this morphine-induced stereotypic behavior persists with some interruption for a time of two to three hours. As described above, the behavior consists of repetitive mouthing and biting behavior directed toward the grid floor of the enclosure or toward the animal's own paws. Subsequently the behavior can be elicited by administration of a low dose of morphine or of a low dose of a dopamine agonist such as, e.g., amphetamine, as long as 17 months after the stereotypy was initially established. Such re-expressed behavior persists for the duration of the action of the administered morphine or dopamine agonist.

As the animals in Examples 1 and 2 described above never received an opiate agonist, the ability of naloxone both to prevent and to block neuroleptic-mediated stereotypy strongly suggests a role of an endogenous opioid in this behavior. The large dose of naloxone used in the present study does not preclude the possibility that non-opioid systems are involved (Sawynok et al. (1979), *Life Sci.*, Vol. 25, pp. 1621–32). However, naloxone's high dose effects in blocking the oral stereotypies described in the present study do not appear to be due to an antagonism of central dopaminergic systems. Indeed, high doses of naloxone (10–30 mg/kg) do not antagonize amphetamine-induced circling behavior in rats with unilateral 6-hydroxydopamine lesions, whereas lower doses of the opiate antagonist (0.3–3.0 mg/kg) do not block the amphetamine effect (Dettmar et al. (1978), *Neuropharmacol.*, Vol. 17, pp. 1041–44). The phenomenological similarity between morphine-induced oral stereotypy (Pollock et al. (1989), *Neurosci. Lett.*, Vol. 10, pp. 291–96), and neuroleptic-mediated oral stereotypy (described by Tarsy et al. (1974)), and the fact that neuroleptics can block morphine-induced stereotypy (Pollock et al. (1989)), favors an hypothesis that an opioid system is involved in the etiology of this dyskinesia.

The dopamine receptor supersensitivity model has been criticized on numerous grounds. There is a lack of concordance in timing between dopamine biochemical changes and incidence of oral stereotypy (Christenson et al. (1976), *Psychopharmacology*, Vol. 48, pp. 1–6); dopamine receptor agonists do not always exacerbate the symptoms of TD (Haggstrom et al. (1982), *Pharmacopsychiatria*, Vol. 15, pp. 161–63); there is no apparent change in the number or binding affinity of ligands to dopamine D1 or D2 receptors in the brains of patients with TD (Crow et al. (1982), *Jour. Clin. Psychopharmacol.*, Vol. 82, pp. 336–40); and there is no difference in basal prolactin levels between schizophrenics having TD and those not having TD (Tripodianakis et al. (1983), *Biol. Psychiatry*, Vol. 18, pp. 337–45). These problems notwithstanding, the animal model defined by the production of oral stereotypy following chronic neuroleptic treatment (Ellison et al. (1989)) or defined by challenge with a low dose of a dopamine receptor agonist (Tarsy et al. (1974)) remains a valuable tool. The value of the model rests not necessarily on its suggestion that dopaminergic mechanisms are exclusively involved in the behavior; rather, the physical behavior observed in the animal homolog warrants a closer study of the neurochemical/receptor changes associated with chronic haloperidol treatment and how these changes may be influenced by an opiate antagonist.

As the following Example shows, opiate antagonists can be used according to the invention to suppress dyskinesia associated with Huntington's Disease.

Example 5

Opiate Antagonists can be used in Treatment of the Dyskinesia Associated with Huntington's Disease.

Huntington's Disease results in a chorea in which one of the major manifestations is a repetitive chewing-like movement of the mouth. These manifestations may be a consequence of an upregulation of endogenous dopamine in the extrapyramidal motor system (in particular the striatum, i.e., caudate nucleus and putamen), the system most involved with the control of fine motor movements. The dyskinesia associated with HD can be attenuated by administration of a specific opiate antagonist according to the invention, as shown in the following example.

Thirteen patients diagnosed as having Huntington's Disease ("HD patients") receive naltrexone in a continuing treatment regimen, as follows. Two of the patients have very advanced HD, three have the rigid form of HD, and eight have choreiform HD. Naltrexone was administered orally to each patient, in doses between 50 mg twice daily and, at maximum, 50 mg five times daily; the optimum dose appeared to be 50 mg 3 to 4 times daily. No objectionable effects were reported, apart from nausea reported in rare instance following administration of the medication on an empty stomach. CBC and blood chemistry profile with liver function tests remained normal in all patients. No effect of such treatment was distinguishable in the patients with advanced HD, and the naltrexone treatment in these patients was discontinued. The patients having the rigid form of HD show either no distinguishable effect or an aggravation of their symptoms, and the naltrexone treatment in these patients, too, was discontinued. All the patients having choreiform HD reported a decrease in their choreiform movements, confirmable by neurological examination, and an improvement in speech. In most patients the improvement began early in the course of treatment, and the treatment has continued for three to about ten months. In one patient no improvement appeared early in treatment; naltrexone administration was discontinued in this patient for a time and then resumed, whereupon a detectable decrease in dyskinesia followed.

Naltrexone is at present approved for use only for blockade of the pharmacological effects of exogenously administered opioids and as an adjunct to the maintenance of the opioid free state in detoxified opioid dependent individuals. Naltrexone has few known intrinsic actions besides its opioid blocking properties. Naltrexone can cause an increase in transaminase levels, but no other signs of hepatotoxicity have been observed. Daily treatment of HD patients can result in a decrease in the chorea associated with the disease.

Use

The method of the invention can be used to treat any of a variety of hyperkinetic movement disorders, including drug-induced stereotypies (Tardive Dyskinesia) as well as dyskinesias of psychogenic, idiopathic, genetic, or infectious origin. Treatment according to the invention can be effective not only in reducing already-manifested stereotypic behaviors, but also in preventive suppression of stereotypies in subjects that are at risk for developing such conditions before such symptoms appear.

Dosage regimes can be adjusted according to the response of the particular subject being treated, according to protocols generally recognized in clinical psychopharmacology. For example, satisfactory results can be obtained in treating choreiform movements of HD by administering about 50 mg in a thrice-daily regime. Repeated opiate receptor antagonist administration may result in up-regulating the patient's opiate receptors, rendering them more active and, possibly, resulting in an undesirable increased sensitivity to the patient's endogenous dopamine. Higher or lower doses may be satisfactory, and less frequent administration (such as, for example, once daily or each three days) may give salutory results and reduce any likelihood of up-regulating the opiate receptor system. For this reason, chronic daily administration may be less preferred than less frequent administration.

OTHER EMBODIMENTS

For some treatment regimes, opiate receptor antagonists are preferred that can be administered orally rather than by injection or infusion, and whose effects in suppressing the hyperkinetic movement disorder (or tardive dyskinesia) persist for longer periods following administration, such as naltrexone. Other opiate receptor antagonists may be used. For example, the relatively receptor-nonspecific opiate antagonist nalmefene may be used; or the relatively receptor-specific (δ) opiate receptor antagonist naltrindole may be used. Nalmefene and naltrindole can be administered parenterally; most other relatively specific opiate receptor antagonists do not pass the blood/brain barrier, and so may be less preferred because they must be administered intracerebrally rather than parenterally or orally.

A particular opiate receptor antagonist may, in an indicated treatment protocol, be administered one or more times daily, or less frequently. Either opiate receptor antagonist or neuroleptic can be administered orally, or by injection, or by infusion, for example. An administration of the opiate receptor antagonist may be complete prior to the beginning of an administration of the neuroleptic, or an administration of the neuroleptic may begin during the time in which the opiate receptor antagonist is administered.

What is claimed is:

1. A method for preventing neuroleptic-induced tardive dyskinesia in a subject, in whom neuroleptic treatment is indicated but who has not received a neuroleptic, comprising
commencing administration of an effective dose of an opiate receptor antagonist, said antagonist selected from the group consisting of naltrexone, naloxone, nalmefene, and naltrindole, to the subject concurrently with the commencement of administration of a neuroleptic prior to appearance of symptoms of hyperkinesia.

2. The method of claim 1 wherein said opiate receptor antagonist is administered to the subject parenterally.

3. The method of claim 1 wherein said opiate receptor antagonist is administered to the subject orally.

4. A method for preventing a genetic hyperkinetic movement disorder in a subject, the subject having a genetic disorder that leads to the genetic hyperkinetic movement disorder, comprising administering to the subject, prior to appearance of symptoms of hyperkinesia associated with said disorder, an effective dose of an opiate receptor antagonist, said antagonist selected from the group consisting of naltrexone, naloxone, nalmefene, and naltrindole.

5. A method for preventing a hyperkinetic movement disorder in a subject who is predisposed to Huntington's disease, comprising administering to said subject a therapeutically effective dose of an opiate receptor antagonist, said antagonist selected from the group consisting of naltrexone, naloxone, nalmefene, and naltrindole, prior to appearance of symptoms of hyperkinesia associated with said disorder.

6. A method for treating a genetic hyperkinetic movement disorder in a subject, comprising administering to the subject an effective dose of an opiate receptor antagonist, said antagonist selected from the group consisting of naltrexone, naloxone, nalmefene, and naltrindole.

7. The method of claim 4 or 6 wherein said opiate receptor antagonist is administered to the subject parenterally.

8. The method of claim 4 or 6 wherein said opiate receptor antagonist is administered to the subject orally.

9. A method for treating or preventing choreiform movements in a subject having Huntington's Disease, comprising
administering to said subject an effective dose of an opiate receptor antagonist, said antagonist selected from the group consisting of naltrexone, naloxone, nalmefene, and naltrindole.

10. The method of claim 9 wherein said opiate receptor antagonist is administered to the subject parenterally.

11. The method of claim 9 wherein said opiate receptor antagonist is administered to the subject orally.

12. A method for preventing the appearance of an idiopathic hyperkinetic movement disorder in a subject, comprising
identifying a subject who has an idiopathic disorder that leads to a hyperkinetic movement disorder, and
administering an effective dose of an opiate receptor antagonist, said antagonist selected from the group consisting of naltrexone, naloxone, nalmefene, and naltrindole, to said subject prior to appearance of symptoms of hyperkinesia associated with said disorder.

13. A method for treating an idiopathic hyperkinetic movement disorder in a subject, comprising
identifying a subject having an idiopathic hyperkinetic movement disorder, and
administering an effective dose of an opiate receptor antagonist, said antagonist selected from the group consisting of naltrexone, naloxone, nalmefene, and naltrindole, to said subject having an idiopathic movement disorder.

14. A method for preventing the appearance of a psychogenic hyperkinetic movement disorder in a subject, comprising
identifying a subject who has a psychogenic disorder that leads to a hyperkinetic movement disorder, and
administering an effective dose of an opiate receptor antagonist, said opiate receptor antagonist selected from the group consisting of naloxone, naltrexone, nalmefene and naltrindole, to said subject prior to appearance of symptoms of hyperkinesia associated with said disorder.

15. A method for treating a psychogenic hyperkinetic movement disorder in a subject, comprising
identifying a subject having a psychogenic movement disorder, and
administering an effective dose of an opiate receptor antagonist, said antagonist selected from the group consisting of naltrexone, naloxone, nalmefene, and naltrindole, to said subject having a psychogenic movement disorder.

16. The method of claim 12, 13, 14, or 15 wherein said opiate receptor antagonist is administered to the subject parenterally.

17. The method of claim 12, 13, 14, or 15 wherein said opiate receptor antagonist is administered to the subject orally.

* * * * *

UNITED STATES PATENT AND TRADEMARK OFFICE
CERTIFICATE OF CORRECTION

PATENT NO. : 6,153,620
DATED : November 28, 2000
INVENTOR(S) : Kornetsky, C

It is certified that error appears in the above-identified patent and that said Letters Patent is hereby corrected as shown below:

Column 1,
Line 6, please replace "The invention was made in the course of work supported in part by U.S. Government funds, and the Government has certain rights in the invention" with -- This invention was made with government support under DA02326 and DA00099, awarded by the National Institutes of Health. The United States Government has certain rights in the invention. --

Signed and Sealed this

Seventh Day of May, 2002

*Attest:*

JAMES E. ROGAN
*Attesting Officer*     *Director of the United States Patent and Trademark Office*